United States Patent [19]
Kendall

[11] Patent Number: 4,770,659
[45] Date of Patent: Sep. 13, 1988

[54] FEMORAL PROSTHESIS WITH FORCED MOTION SHARING

[76] Inventor: Richard L. Kendall, 8707 Falmouth Ave., Playa Del Rey, Calif. 90291

[21] Appl. No.: 23,904

[22] Filed: Mar. 9, 1987

Related U.S. Application Data

[63] Continuation of Ser. No. 587,312, Mar. 7, 1984, abandoned.

[51] Int. Cl.$^4$ .................................................. A61F 2/34
[52] U.S. Cl. ........................................................ 623/22
[58] Field of Search ............................. 623/22, 23, 16

[56] References Cited

U.S. PATENT DOCUMENTS

| | | |
|---|---|---|
| 3,813,699 | 6/1974 | Giliberty . |
| 3,863,273 | 2/1975 | Averill ................................ 623/22 |
| 4,004,300 | 1/1977 | English ............................... 623/22 |
| 4,044,403 | 8/1977 | D'Errico . |
| 4,172,296 | 10/1979 | D'Errico . |
| 4,241,463 | 12/1980 | Khovaylo . |

FOREIGN PATENT DOCUMENTS

| | | | |
|---|---|---|---|
| 2911754 | 11/1980 | Fed. Rep. of Germany | ........ 623/22 |
| 2950536 | 7/1981 | Fed. Rep. of Germany | ........ 623/22 |

Primary Examiner—Richard J. Apley
Assistant Examiner—David J. Isabella
Attorney, Agent, or Firm—Gordon L. Peterson

[57] ABSTRACT

A hip joint prosthesis which provides for universal motion about three transverse pivot axes comprising a femoral member adapted to be coupled to the femur and a cup assembly partially receiving the femoral member. The cup assembly is slidably received in the acetabulum. Motion about one of the pivot axes can occur in the prosthesis, and motion about the other two pivot axes is forced to occur between the cup assembly and the acetabulum. The cup assembly includes an insert which is snap-fit within a cap. The insert is of one-piece, integral construction and has a resilient, flexible portion for allowing a portion of the femoral member to be received within a cavity of the insert.

14 Claims, 2 Drawing Sheets

FEMORAL PROSTHESIS WITH FORCED MOTION SHARING

This application is a continuation of application Ser. No. 587,312 filed Mar. 7, 1984 now abandoned.

BACKGROUND OF THE INVENTION

The joints of a human skeletal structure typically comprise a ball and a socket. Joints, such as the hip and shoulder, provide for universal motion, i.e, relative motion about three transverse pivot axes.

For example, a hip joint includes a femoral head which is joined to the proximal femur by a neck which is angularly disposed relative to the axis of the femur and relative to the vertical axis of the human body. A natural socket or acetabulum receives the femoral head and cooperates therewith to form a universal joint which permits relative motion about three transverse pivot axes.

Various progressive diseases, such as osteoarthritis, can bring about deterioration of the natural socket and/or the natural femoral head. When this occurs, the diseased component can be replaced or rebuilt using an appropriate prosthetic device.

For example, in total hip replacement, an acetabular cup is cemented into the acetabulum, and the natural femoral head and neck are removed. A femoral member comprising an elongated stem, a neck and a head is mounted within the proximal femur be cementing of the stem into the femur. The head is received in the cup to provide the desired universal motion. One example of this construction is shown in Chambers U.S Pat. No. 3,656,184.

In another form of total hip replacement, a femoral cup is mounted on the head of the prosthetic femoral member. One construction of this type is shown by way of example in Averill U.S. Pat. No. 3,863,273. In this construction, the head is mounted within the femoral cup for universal movement, and the femoral cup is mounted for universal movement within the acetabulum. Accordingly, as the hip joint is used, the motion may be accommodated by either or both of these interfaces. Unfortunately, a pseudocapsule may form and impede the movement of the femoral cup in the acetabulum. In this event, motion occurs primarily or entirely between the head and the femoral cup, and this can accelerate deterioration of the cartilage by uneven lubrication between the femoral cup and the natural acetabulum and the creation of local stresses in the natural acetabulum due to the lack of relative movement between the femoral cup and the natural acetabulum.

Oh application Ser. No. 340,027 filed Jan. 18, 1982, overcomes this problem by providing a hip joint prosthesis in which some of the universal motion of the joint is forced to occur in the natural socket. Because the motion is forcibly shared between the prosthesis and the natural socket, the femoral component does not become locked in the natural acetabulum, and much more even lubrication of the acetabulum occurs.

The forced motion-sharing concept is very sound. Unfortunately, the cup assembly which provides the forced motion-sharing comprises four separate components, and these components are not as easy to assemble as is desired. More specifically, in the construction of the prior application, the cup assembly includes an insert comprising three separate components which are threadedly retained within a cup or cap. It was believed that threading was necessary in order to provide the desired strong securement between the components of the insert and the cup.

SUMMARY OF THE INVENTION

This invention provides a femoral endoprosthesis conversion with forced motion sharing which comprises fewer parts and is much easier to assembly than the prior art forced motion-sharing prosthesis. Thus, all of the advantages of forced motion are obtainable in a prosthesis which is relatively easy to manufacture and assemble. The assembly and simplification advantages are obtained with this invention without sacrificing any of the desirable features of forced motion sharing.

Universal motion may be considered as motion about three transverse axes. With this invention, motion in the natural socket is forced to occur by permitting the prosthesis to accommodate motion about no more than about two of the three transverse axes. Accordingly, motion about at least a third of the axes is forced to occur between the prosthesis and the natural socket.

It it preferred to have most of the universal motion occur in the natural socket. Accordingly, the prosthesis preferably provides for motion about only one of the three transverse axes. More particularly, the prosthesis can conveniently accommodate motion about an axis extending generally along, or parallel to, the axis of the neck of the prosthesis.

This invention is applicable, for example, to a prosthesis which includes a head adapted to be coupled to a bone and a cup assembly. With this invention, the construction is greatly simplified, without sacrificing any of the desirable functions, by providing a cup assembly that includes an insert of one-piece integral construction and a cap. Thus, in a preferred construction, the cup assembly includes only two members, i.e., the insert and the cap.

The insert has an interior surface defining a cavity, and the cavity is adapted to receive and slidably cooperate with the head of the femoral component. To enable the head to be inserted into the cavity, the insert includes a resilient flexible portion which allows the head to be šnap-fit into the cavity.

The desired flexibility of the insert to permit receipt of the femoral head can be provided in different ways. However, preferably the insert has a skirt at one end, and the skirt is segmented to at least partially define the resilient, flexible portion.

The cap has an interior surface defining a cavity for receiving the insert and an exterior surface. At least a portion of the exterior surface is generally spherical and adapted to be slidably received in a natural socket of the joint.

Another advantage of this invention is the elimination of the screw threads between the insert and the cap. With this invention, the insert is attached to the cap by attaching means which includes means for snap-fitting the cap on the insert. This can advantageously be accomplished by an interlocking groove and recess on the cap and the insert. In a preferred construction, the projection is on the interior surface of the cap and, to more distinctly define the projection, it preferably has a groove extending along its inner longitudinal edge.

The prosthesis of this invention can provide forced motion sharing in various different ways. However, preferably this is accomplished, at least in part, by cooperating conical surfaces on the head and on the interior surface of the cavity of the insert which allow the head to pivot about one axis relative to the exterior surface of the cap. The conical surface of the insert can advantageously be at least along the interior surface of the skirt. Such conical surface extends radially inwardly as it extends away from a spherical portion of the insert. This radially thickens at least portions of the segments so they can provide a strong bearing surface. Preferably the skirt has the thickest radial portion of the insert.

The invention, together with additional features and advantages thereof, may best be understood by reference to the following description taken in conjunction with the accompanying illustrative drawing.

DESCRIPTION OF THE PREFERRED EMBODIMENTS

Figure 1:
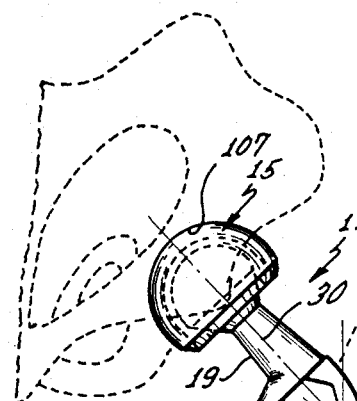
FIG. 1 is a frontal elevational view showing a femoral endoprosthesis conversion constructed in accordance with the teachings of this invention and a portion of the natural pelvis, acetabulum and femur.

FIG. 1 shows a hip joint prosthesis 11 in the form of a femoral endoprosthesis conversion. The prosthesis 11 includes a femoral member or component 13 and a femoral cup assembly 15. The femoral member 13 is preferably intergrally constructed of a biocompatible metal, such as ultra high strength, cold-worked and aged, wrought cobalt chromium nickel alloy. This alloy is preferred because of its high fatigue strength. Generally, the femoral member 13 is configured similarly to the proximal femur.

Figure 2:
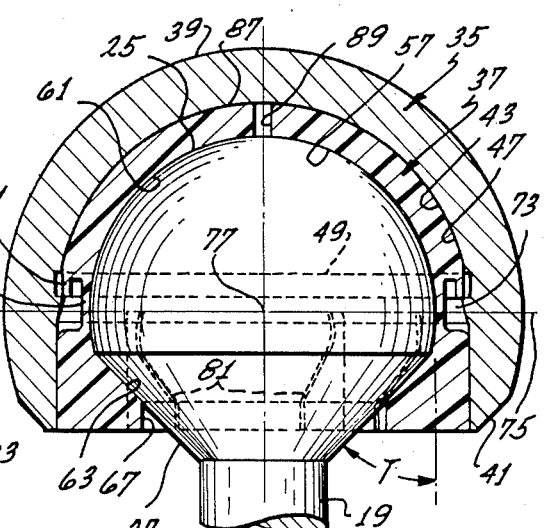
FIG. 2 is a fragmentary, axial, sectional view taken on an axial plane through the cup assembly, head and a portion of the neck of the prosthesis.
Figure 4:
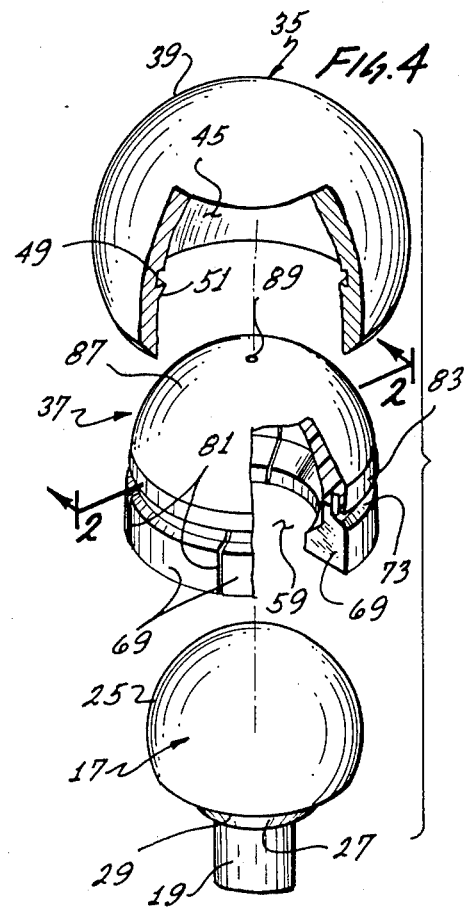
FIG. 4 is an exploded sectional view of the cup assembly and a portion of the head and neck.

The femoral member 13 comprises a head 17, a neck 19 and a stem 21 joined to the head by the neck, and a collar 23 around the neck near its juncture with the stem. As shown in FIG. 4, the head 17 has a spherical surface 25 and a conical surface 27 which intersects the spherical surface along a circular line 29. In the embodiment illustrated, the spherical surface 25 extends for over 180 degrees, and the axis of the conical surface 27 passes through the center of the spherical surface 25. The surfaces 25 and 27 are smooth and polished, and the major diameter of the conical surface 27 is substantially equal to the diameter of the circular line 29. The conical surface 27 has an angle of taper "T" (FIG. 2) which may be, for example, 50 degrees. The neck 19, which preferably extends generally linearly, has an axis 30 which is coaxial with the axis of the conical surface 27 and which passes through the center of the spherical surface 25. The neck 19 is cylindrical at least at regions thereof which are adjacent the conical surface 27.

The stem 21 is elongated and has identical, elongated grooves 31 (only one being shown in FIG. 1) extending axially thereof on opposite sides of the stem. Identical fins 33 extend distally along a curved portion of the stem 21 from the collar 23 along opposite sides of the stem.

The cup assembly 15 includes a cap 35 and an insert 37. The cap 35 is preferably constructed of a biocompatible metal and has a smooth, exterior surface comprising a spherical exterior surface 39, which extends for over 180 degrees, and a relatively small conical exterior surface 41 which intersects the spherical exterior surface. The cap 35 also has an interior surface 43 which defines an open-ended cavity 45. The interior surface 43 has a spherical surface 47 of slightly less than hemispherical size, a cylindrical groove 49 (FIG. 3) contiguous the spherical surface, an annular, sloping projection or rib 51 which terminates inwardly in a shoulder 53 defined by the groove 49 and a cylindrical surface 55 contiguous the outer edge of the projection 51. The groove 49 and the cylindrical surface 55 are coaxial and of equal diameter and are also coaxial with the spherical surface 47. The spherical surface 47 is of slightly lesser diameter than the cylindrical groove 49 and the cylindrical surface 55.

The insert 37 is of one-piece integral construction and is preferably, integrally molded from a suitable plastic material, such as ultra-high molecular weight polyethylene. The insert 37 has an interior surface 57 defining an open-ended cavity 59. The interior surface 57 comprises a spherical surface 61 of slightly greater than hemispherical configuration and a conical surface 63 which intersects the spherical surface 61 along a circular line and which extends radially inwardly as it extends axially away from the spherical surface. The spherical surface 61 and the conical surface 63 are sized and configured to receive, and slidably cooperate with, the spherical surface 25 and the conical surface 27, respectively, of the head 17. The interior surface 57 also includes a cylindrical surface 67 coaxial with the conical surface 63 and having a diameter equal to the minor diameter of the conical surface.

Figure 3:
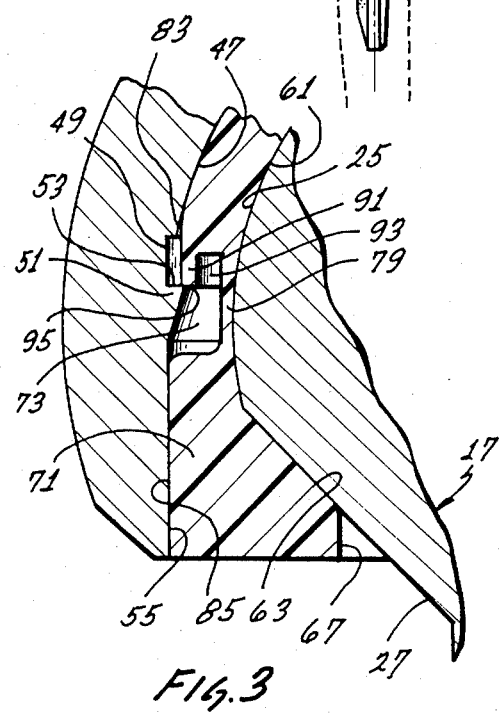
FIG. 3 is an enlarged, fragmentary, sectional view of a portion of the head, insert and cap.

To enable the head 17 to be snap-fit into the cavity 59, the insert 37 has a resilient, flexible portion. In this preferred embodiment, this comprises resilient, flexible segments 69 in a skirt 71. As shown in FIG. 3, the insert 37 terminates at one end in the skirt 71, and the skirt 71 may be considered as that portion of the insert at and below a continuous circumferentially extending exterior groove 73. The center of the groove 73 lies along a diametrical line 75 which extends through the center 77 of the spherical surface 61. The center 77 of the spherical surface 61 lies on the axis of the conical surface 63. The groove 73 defines a thin, flexible, resilient web 79 (FIG. 3) which enables the segments 69 to flex resiliently radially outwardly. The segments 69 are defined by very narrow cuts or slots 81 in the skirt. Each of the slits 81 preferably extends to the line 75. Thus, the insert 37 is provided with flexibility at least to the portion of the interior surface 57 which lies below the line 75.

Because the conical surface 63 extends radially inwardly as it extends away from the spherical surface 61, the skirt has the thickest radial portion of the insert. This provides a strong bearing surface for the head 17. In addition, the cylindrical surface 67 forms a bearing surface for the proximal portion for the neck 19, which is also cylindrical and slidably receivable by the cylindrical surface 67.

To enable the cap 35 to be slid over the insert 37, the insert has external cylindrical surfaces 83 and 85 on opposite sides of the grooves 73, and to permit the insert to be snugly received within the cap 37 in close mating relationship, the insert has an external spherical surface 87 adapted to be snugly received in the spherical surface 47 of the cap. To provide for the escape of air between the cap 35 and the insert 37 during assembly, the insert 37 has an aperture 89 at the central polar region of the insert.

To facilitate assembly, the insert 37 has an annular undercut flange 91 with an undercut 93 communicating with the groove 73 to permit the flange to flex resiliently radially inwardly. The flange 91 terminates downwardly in a shoulder 95.

The insert 37 can be easily assembled onto the femoral member 13 by forcing it over the head 17. The segments 69 flex resiliently radially outwardly to permit the insert 37 to be snap-fit onto the head 17. Next, the cap 35 is snap-fit onto the insert 37. This retains the segments 69 against radial outward movement and securely retains the head 17 within the cup assembly 15.

The cap 37 and the insert 37 can be easily assembled by forcing the cap down over the insert. During this time, the air from between the insert 37 and the cap 35 escapes through the aperture 89. The sloping rib 51 cams the flange 91 inwardly to allow the rib to more easily pass the flange and enter the groove 73. In this position, the groove 73, which is partially defined by the shoulder 95, interlocks with the projection 51. In this manner, the cap is snap-fit onto the insert.

In the assembly condition, all of the spherical surfaces of the cup assembly 15 and the head 17 are concentric, and the conical surfaces 27 and 63, the cylindrical surface 67 and the axis 30 of the neck 19 are coaxial. The conical surfaces 27 and 63 cooperate to permit rotational movement of the head 17 relative to the cup assembly 15 only about the axes of the conical surfaces.

As shown in FIG. 1, the stem 21 can be installed in a femur 101 using known surgical procedures. Generally, the stem 21 is retained in the intermedullary canal 103 of the femur by a suitable cement, and the collar 23 rests on a proximal surface of the femur. The cup assembly 15 is slidably received in the natural hip socket or acetabulum 107.

In use, the joint formed by the acetabulum 107 and the prosthesis 11 must accommodate universal motion, i.e., motion about three transverse pivot axes. The head 17 slides within the insert 37 as allowed by the conical surfaces 27 and 63 to provide pivotal motion about the axis 30 of the neck 19. Because this is the only pivotal motion to be accommodated by the prosthesis 11, all other pivotal motion must occur as a result of sliding contact between the acetabulum and the spherical exterior surface 39 of the cup assembly 15. Thus, motion about the other two transverse pivot axes is forced to occur within the acetabulum 107.

If the disease progresses, it may eventually be necessary to provide an acetabular cup (not shown) in the acetabulum 107. When this occurs, the cup assembly 15 is removed from the femoral member 13 to expose the head 17, and the head 17 is inserted into the acetabulur cup for universal pivotal motion relative thereto. This can be accomplished without removing the femoral member 13 from the femur 101.

Figure 5:
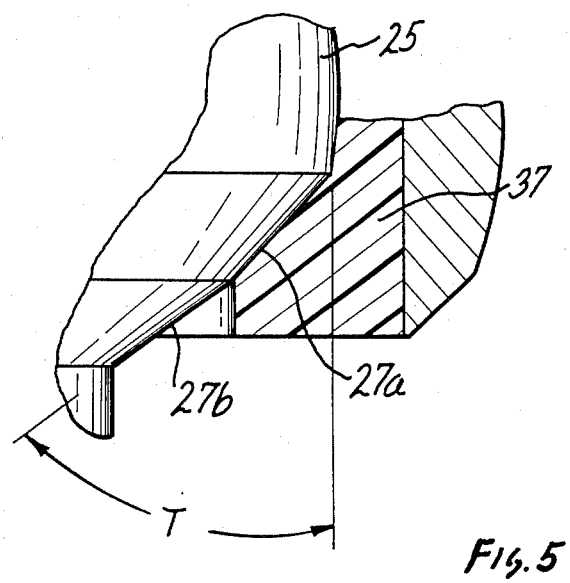
FIG. 5 is a fragmentary sectional view similar to a portion of FIG. 2 showing another embodiment of the invention.

In an alternative construction of FIG. 5, the conical surface 27 includes a first highly polished conical surface 27a which intersects the spherical surface 25 and slidably cooperates with the conical surface 63 of the cavity and a second conical surface 27b which intersects the first conical surface. This facilitates blending of the conical surface 27 into the neck 19. To enable lubricant from the body to get between the surface of the head 17 and the insert 37, the angle of taper T (FIGS. 2 and 5) of the second conical surface 27b is preferably slightly, e.g., 6 degrees, greater than the angle of taper T of the first conical surface 27a, and this amount is exaggerated for clarity in FIG. 5. The first conical surface 27a is preferably sufficiently long to cover most or all of the conical surface 63.

Although an exemplary embodiment of the invention has been shown and described, many changes, modifications and substitutions may be made by one having ordinary skill in the art without ncessarily departing from the spirit and scope of this invention.

I claim:

1. A prosthesis comprising:
   a head having an exterior surface, at least a portion of said exterior surface being generally spherical;
   means coupled to said head for use in attaching the head to a bone whereby the head moves with the bone when the head is attached to the bone;
   a cup assembly including an insert and a cap;
   said insert being of one piece integral construction and having an interior surface defining a cavity and a resilient flexible portion for allowing said head to be snap-fit into the cavity, said interior surface of said inserted being adapted to slidably cooperate with said head;
   said cap having an interior surface defining a cavity for receiving said insert and an exterior surface, at least a portion of said exterior surface of said cap being generally spherical and adapted to be slidably received in a natural socket of a joint;
   means for attaching the insert to the cap with the insert being in said cavity of the cap;
   said cup assembly and said head including means for mounting the head within the cavity of the insert for motion relative to the exterior surface of the cap about at least one pivot axis but about fewer pivot axes than is required for universal movement of the bone relative to the natural socket whereby at least some sliding movement between the exterior surface of the cap and the natural socket is forced to occur in order to obtain relative universal movement between the bone and the natural socket;
   the insert having a skirt at one end of the insert, said skirt having means dividing said skirt into separate segments to at least partially define said resilient flexible portion; and
   said attaching means for the insert including a resilient under cut flange on said insert, an external groove on the insert partially defining said flange and at least partially defining a flexible resilient web and an internal rib on the cap receivable in the groove and the segments of said skirt extend to said resilient web and can be flexed radially outwardly to receive the head.

2. A prosthesis as defined in claim 1 wherein said mounting means includes cooperating conical surfaces on said head and said interior surface of said cavity of said insert.

3. A prosthesis as defined in claim 2 wherein said interior surface of said insert includes a cylindrical surface on the side of the conical surface of the insert which is remote from the spherical surface.

4. A prosthesis as defined in claim 1 wherein said interior surface of said insert has a spherical portion, said mounting means includes said interior surface of said insert at least at said skirt being generally conical and extending radially inwardly as it extends away from the spherical portion whereby the segments are radially thickened over at least a portion of their length.

5. A prosthesis as defined in claim 1 including at least one aperture in a polar region of the insert.

6. A prosthesis as defined in claim 1 wherein said interior surface of said cap has a generally cylindrical groove and a generally cylindrical surface, said groove and said cylindrical surface of the cap being spaced apart by said rib.

7. A prosthesis comprising:
a head having an exterior surface, said exterior surface having a generally spherical portion and a generally conical portion with the conical portion intersecting the spherical portion and extending radially inwardly as it extends away from the spherical portion;
means coupled to said head for use in attaching the head to the proximal femur whereby the head moves with the femur when the head is attached to the femur;
a cup assembly including an insert and a cap;
said insert being of one-piece integral construction and having an interior surface defining a cavity, said cavity having a spherical portion and a conical portion with the conical portion intersecting the spherical portion, said insert having a skirt with the conical surface forming at least a portion of the interior surface of the skirt, said skirt having means dividing the skirt to define a plurality of separate resilient segments;
said spherical and conical portions of the cavity being sized to slidably receive the spherical and conical portions of the head, respectively, and said segments being resiliently expandable radially outwardly to allow the cavity to receive said head;
said cap having an interior surface defining a cavity for receiving said insert and an exterior surface, at least a portion of said exterior surface of said cap being generally spherical and adapted to be slidably received in a natural socket of a joint;
means including an interlocking groove and recess for snap-fitting the cap on the insert; and
said conical portion of said head including a first highly polished conical surface which intersects the spherical portion of the head and slidably cooperates with the conical portion of the cavity and a second conical surface intersecting the first conical surface and said first and second conical surface have different angles of taper.

8. A prosthesis as defined in claim 7 wherein the second conical surface has a greater angle of taper than the first conical surface.

9. A prosthesis comprising:
a head having an exterior surface, said exterior surface having a generally shperical portion and a generally conical portion with the conical portion intersecting the spherical portion and extending radially inwardly as it extends away from the sperhical portion;
means coupled to said head for use in attaching the head to the proximal femur whereby the head moves with the femur when the head is attached to the femur;
a cup assembly including an insert and a cap;
said insert being of one-piece integral construction and having an interior surface defining a cavity, said cavity having a spherical portion and a conical portion with the conical portion intersecting the spherical portion, said insert having a skirt with the conical surface forming at least a portion of the interior surface of the skirt, said skirt being divided to define a plurality of resilient segments;
said cap having an interior surface defining a cavity for receiving said insert and an exterior surface, at least a portion of said exterior surface of said cap being generally spherical and adapted to be slidably received in a natural socket of a joint;
means for retaining the cap on the insert;
said spherical and conical portions of the cavity being sized to slidably receive the spherical and conical portions of the head, respectively, whereby the head is mounted for motion relative to the exterior surface of the cap about at least one pivot axis but about fewer pivot axes than is required for universal movement and said segments being resiliently expandable radially outwardly to allow the cavity to receive said head; and
said retaining means including an internal rib on the interior surface of the cap and an undercut flange on the insert which is engageable with said internal rib, said interior surface of said cap having a groove and a generally cylindrical surface on opposite sides of the internal rib, said insert having an external groove defining said flange and defining a resilient web which enables said segments to be resiliently expandable radially outwardly and the segments of the skirt extend to the resilient web.

10. A prosthesis comprising:
a head of metal having an exterior surface, said exterior surface having a generally spherical portion and a generally conical portion with the conical portion intersecting the spherical portion and extending radially inwardly as it extends away from the spherical portion;
means including a stem coupled to said head for use in attaching the head to the proximal femur whereby the head moves with the femur when the head is attached to the femur;
a cup assembly including a plastic insert and a metal cap;
said insert being of one-piece integral construction and having an interior surface defining a cavity, said cavity having a spherical portion, a cylindrical portion and a conical portion with the conical portion intersecting the spherical portion and the cylindrical portion, said conical portion being intermediate the spherical and cylindrical portions and extending radially inwardly as it extends axially away from the spherical portion, said insert having a skirt with the conical surface forming at least a portion of the interior surface of the skirt, said skirt being divided to define a plurality of resilient segments;
said spherical and conical portions of the cavity being sized to slidably receive the spherical and conical portions of the head, respectively, and said segments being resiliently expandable radially outwardly to allow the cavity to receive said head;
said cap having an interIor surface defining a cavity for receiving said insert and an exterior surface, at least a portion of said exterior surface of said cap being generally spherical and adapted to be slidably received in a natural socket of a joint; and
means for snap-fitting the cap on the insert.

11. A prosthesis as defined in claim 10 wherein said snap-fitting means includes an internal rib on the interior surface of the cap and an undercut flange on the insert which is engageable with said internal rib, said interior surface of said cap having a groove and a generally cylindrical surface on opposite sides of the internal rib, said insert having an external groove partially defining said flange and defining a resilient web which enables said segments to be resiliently expandable radially outwardly and the segments of the skirt extend to said resilient web.

12. A prosthesis comprising:

a head having an exterior surface, at least a portion of said exterior surface being generally spherical;

means coupled to said head for use in attaching the head to a bone whereby the head moves with the bone when the head is attached to the bone;

a cup assembly including an insert and a cap;

said insert being of one piece integral construction and having an interior surface defining a cavity and a resilient flexible portion for allowing said head to be snap-fit into the cavity, said interior surface of said insert being adapted to slidably cooperate with said head;

said cap having an interior surface defining a cavity for receiving said insert and an exterior surface, at least a portion of said exterior surface of said cap being generally spherical and adapted to be slidably received in a natural socket of a joint;

means for attaching the insert to the cap with the insert being in said cavity of the cap;

said cup assembly and said head including means for mounting the head within the cavity of the insert for motion relative to the exterior surface of the cap about at least one pivot axis but about fewer pivot axes than is required for universal movement of the bone relative to the natural socket whereby at least some sliding movement between the exterior surface of the cap and the natural socket is forced to occur in order to obtain relative universal movement between the bone and the natural socket;

the insert having a skirt at one end of the insert, said skirt having means dividing said skirt into separate segments to at least partially define said resilient flexible portion; and said interior surface of said insert including a cylindrical surface on the side of the conical surface of the insert which is remote from the spherical surface.

13. A prosthesis as defined in claim 12 wherein the insert has a skirt at one end of the insert and said skirt has the thickest radial portion of the insert.

14. A prosthesis as defined in claim 12 wherein said attaching means for the insert includes means for snap-fitting the cap on the insert.

* * * * *